United States Patent
Iijima

(10) Patent No.: US 12,133,735 B2
(45) Date of Patent: Nov. 5, 2024

(54) ELECTRODE CATHETER

(71) Applicant: JAPAN LIFELINE CO., LTD., Tokyo (JP)

(72) Inventor: Yuto Iijima, Tokyo (JP)

(73) Assignee: JAPAN LIFELINE CO., LTD., Tokyo (JP)

( * ) Notice: Subject to any disclaimer, the term of this patent is extended or adjusted under 35 U.S.C. 154(b) by 530 days.

(21) Appl. No.: 17/310,795

(22) PCT Filed: Mar. 26, 2019

(86) PCT No.: PCT/JP2019/012885
§ 371 (c)(1),
(2) Date: Aug. 24, 2021

(87) PCT Pub. No.: WO2020/194511
PCT Pub. Date: Oct. 1, 2020

(65) Prior Publication Data
US 2022/0133203 A1    May 5, 2022

(51) Int. Cl.
*A61B 5/283* (2021.01)
*A61B 5/00* (2006.01)

(52) U.S. Cl.
CPC ............ *A61B 5/283* (2021.01); *A61B 5/6852* (2013.01); *A61B 2560/0468* (2013.01)

(58) Field of Classification Search
CPC ........... A61B 5/25; A61B 5/287; A61B 5/293; A61B 5/6859; A61B 18/1492;
(Continued)

(56) References Cited

U.S. PATENT DOCUMENTS

2003/0125614 A1   7/2003  Fuimaono et al.
2017/0100187 A1   4/2017  Basu et al.
(Continued)

FOREIGN PATENT DOCUMENTS

EP    3178516 A1   6/2017
EP    3345562 A1   7/2018
(Continued)

OTHER PUBLICATIONS

European Paten Office, an extended European search report issued on Aug. 19, 2022 for European application No. 19921803.3, 8 pages.
(Continued)

*Primary Examiner* — Eun Hwa Kim
(74) *Attorney, Agent, or Firm* — MASUVALLEY & PARTNERS; Peter Martinez

(57) ABSTRACT

To prevent unintended concentration of radially protruding arm members. An electrode catheter (1) includes a catheter body (10) and an electrode unit (100) attached to a distal-end portion (10a) of the catheter body. The electrode unit includes a plurality of arm members (110) in which a one-end portion (110a) in a longitudinal direction is supported by the catheter body and the other-end portion (110b) in a longitudinal direction radially protrudes from the distal-end portion of the catheter body, ring-shaped electrodes (120) attached to the arm members, and core wires (130) as regulating units that regulate actions of adjacent ones of the arm members.

3 Claims, 4 Drawing Sheets

(58) Field of Classification Search
CPC .......... A61B 2018/00375; A61B 2018/00386; A61B 2018/00357
See application file for complete search history.

(56) References Cited

U.S. PATENT DOCUMENTS

| | | | |
|---|---|---|---|
| 2017/0165000 A1* | 6/2017 | Basu | ............. A61B 18/1492 |
| 2017/0281268 A1 | 10/2017 | Tran et al. | |
| 2017/0319269 A1* | 11/2017 | Oliverius | ........... A61B 18/1492 |
| 2018/0184982 A1 | 7/2018 | Basu et al. | |
| 2018/0192904 A1 | 7/2018 | Basu et al. | |
| 2018/0303414 A1* | 10/2018 | Toth | ............. A61N 1/36135 |
| 2019/0183372 A1* | 6/2019 | Ruppersberg | ........ A61B 5/6858 |

FOREIGN PATENT DOCUMENTS

| | | |
|---|---|---|
| JP | 2003-235821 A | 8/2003 |
| JP | 2017-104552 A | 6/2017 |
| JP | 2017-140389 A | 8/2017 |
| JP | 2018-108376 A | 7/2018 |

OTHER PUBLICATIONS

European Paten Office, an Office Action issued on May 17, 2023 for European patent application No. 19921803.3, 4 pages.

Japan Patent Office, an Office Action issued on Apr. 12, 2022 for Japanese patent application No. 2021-508474 with English translation, 6 pages.

WIPO, Japanese International Search Authority, International Search Report (with English translation) and Written Opinion mailed on Jun. 25, 2019 in International Patent Application No. PCT/JP2019/012885, 10 pages.

JPO, Japanese Office Action for Japanese Patent Application No. 2021-508474 mailed on Jul. 19, 2022, 9 pages with English Translation.

\* cited by examiner

ELECTRODE CATHETER

RELATED APPLICATION

This application is the U.S. National Phase of and claims priority to International Patent Application No. PCT/JP2019/012885, International Filing Date Mar. 26, 2019 which is incorporated herein by reference in its entirety.

FIELD

The present invention relates to an electrode catheter suitable for mapping electrical activity in a heart and measuring an intracardiac potential after ablation (cauterization) of the inner wall of the heart.

BACKGROUND

As an electrode catheter for mapping electrical activity in a heart, there is known an electrode catheter having a plurality of arm members that are radially protruding from a distal end of a catheter body (Patent Literature 1).

A terminal electrode and a ring-shaped electrode are attached to each of the arm members of the electrode catheter, and one electrode catheter can collectively and simultaneously measure potentials in a circular region with a radius equal to the length of each arm member in a longitudinal direction of the arm member.

CITATION LIST

Patent Literature

Patent Literature 1: Japanese Patent Application Laid-open No. 2003-235821

SUMMARY

Technical Problem

However, the catheter described in Patent Literature 1 has a problem that arm members are concentrated when a distal-end portion of the catheter rotates around an axial line of the catheter body in a state in which any of the arm members is in contact with an obstacle. As a result, it is not guaranteed that the potential in a circular region is measured in an intended manner.

The present invention has been achieved in view of the above problems, and an object of the present invention is to provide an electrode catheter that can prevent unintended concentration of radially protruding arm members.

Solution to Problem

In order to solve the above problems, the present invention provides an electrode catheter comprising: a catheter body; and an electrode unit attached to a distal-end portion of the catheter body, wherein the electrode unit includes a plurality of arm members in which a one-end portion in a longitudinal direction is supported by the catheter body and the other-end portion in a longitudinal direction radially protrudes from the distal-end portion of the catheter body, electrodes attached to the arm members, and regulating units that regulate actions of adjacent ones of the arm members.

Advantageous Effects of Invention

According to the present invention, since regulating units regulate actions of adjacent arm members, unintended concentration of radially protruding arm members can be prevented.

DESCRIPTION OF EMBODIMENTS

Figure 1:
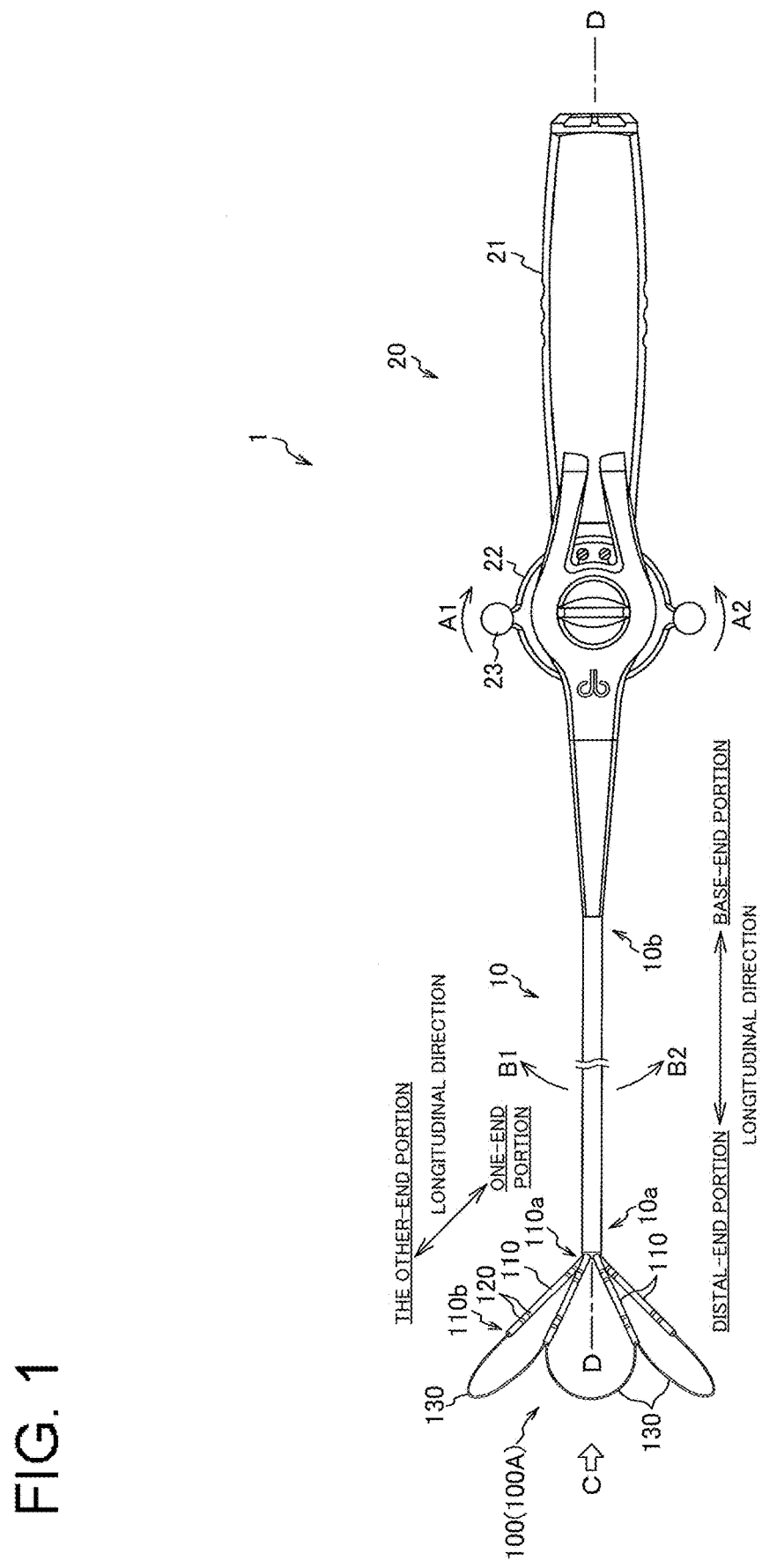
FIG. 1 is a plan view illustrating a schematic configuration of an electrode catheter according to an embodiment of the present invention.

The present invention is described below in detail using embodiments illustrated in the drawings. Note that constituent elements, types, combinations, shapes, and relative arrangements thereof described in the following embodiments are merely explanatory examples and are not intended to limit the scope of the present invention solely thereto unless otherwise specified.

First Embodiment

FIG. 1 is a plan view illustrating a schematic configuration of an electrode catheter according to an embodiment of the present invention.

An electrode catheter 1 is a device that is inserted in a heart through a blood vessel and is used to map electrical activity in the heart and measure an intracardiac potential after ablation (cauterization) of the inner wall of the heart.

The electrode catheter 1 includes a catheter body 10 extending in a longitudinal direction, an operating unit 20 attached to a base-end portion 10b (on a proximal-end side) of the catheter body 10, and an electrode unit 100 (100A) attached to a distal-end portion 10a (on a distal-end side) of the catheter body 10.

<Catheter Body>

The catheter body 10 is formed of a tube-shaped member having at least one lumen 11 (see FIG. 4) extending in a longitudinal direction. A conductive wire (not illustrated) conducted to ring-shaped electrodes 120, 120, onwards constituting the electrode unit 100, a conductive wire (not illustrated) that causes a distal-end-side portion of the catheter body 10 to be curved and deformed (or deflected)

toward directions indicated with arrows B1 and B2 in FIG. 1, and the like are inserted through the lumen 11 of the catheter body 10.

The catheter body 10 is formed of a flexible material. Specifically, synthetic resin such as polyolefin, polyamide, polyether polyamide, polyurethane, nylon, and PEBAX (registered trademark. Substance name: polyether block amide) can be used as the catheter body 10.

The outer diameter of the catheter body 10 is preferably in a range of 1.0 to 3.5 mm and more preferably in a range of 1.6 to 2.8 mm. The length of the catheter body 10 in the longitudinal direction is preferably in a range of 600 to 1500 mm and more preferably in a range of 900 to 1200 mm.

The catheter body 10 may include a perfusion lumen that sprays perfusate from a perfusion port 13 (see FIG. 3) provided at a distal end of the catheter body 10.

<Operating Unit>

The operating unit 20 includes a handle 21 to be gripped by an operator of the electrode catheter 1, a rotating plate 22 that is arranged to be closer to the catheter body 10 than the handle 21 and deflects (or bends and deforms) the distal-end-side portion of the catheter body 10 toward the directions indicated with the arrows B1 and B2 in FIG. 1, and a rotating knob 23 that is operated to rotate the rotating plate 22.

When the rotating plate 22 is rotated toward the direction indicated with an arrow A1 in FIG. 1, the distal-end-side portion of the catheter body 10 is deflected toward the direction indicated with the arrow B1 in FIG. 1 at an angle corresponding to the rotational angle of the rotating plate 22. When the rotating plate 22 is rotated toward the direction indicated with an arrow A2 in FIG. 1, the distal-end-side portion of the catheter body 10 is deflected toward the direction indicated with the arrow B2 in FIG. 1 at an angle corresponding to the rotational angle of the rotating plate 22.

<Electrode Unit>

Figure 2:
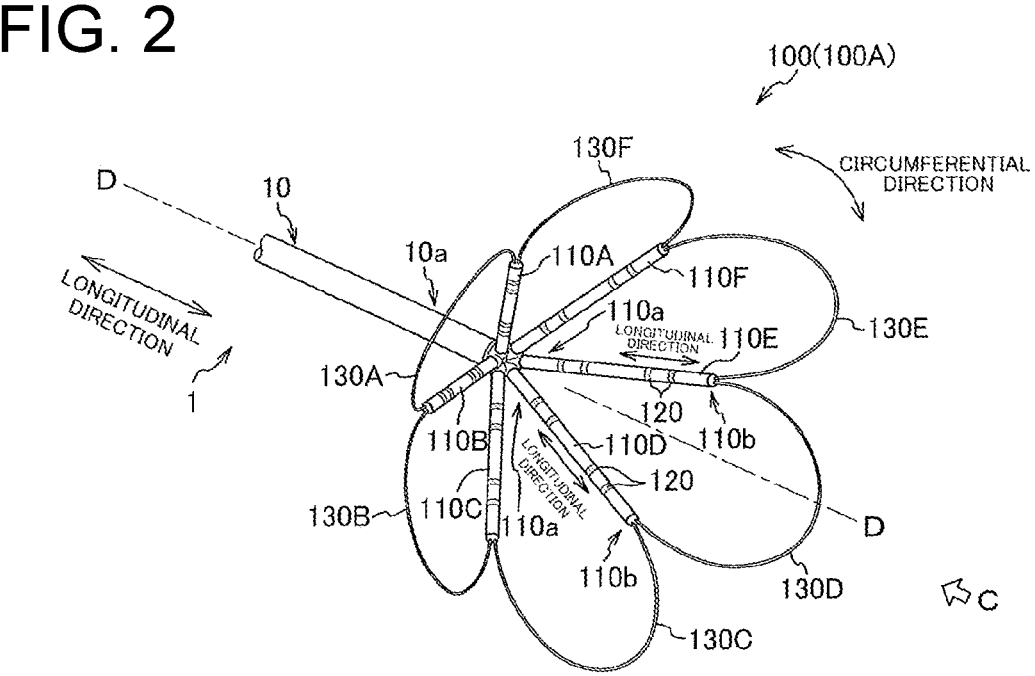
FIG. 2 is a perspective view illustrating a distal-end portion of the electrode catheter illustrated in FIG. 1.
Figure 3:
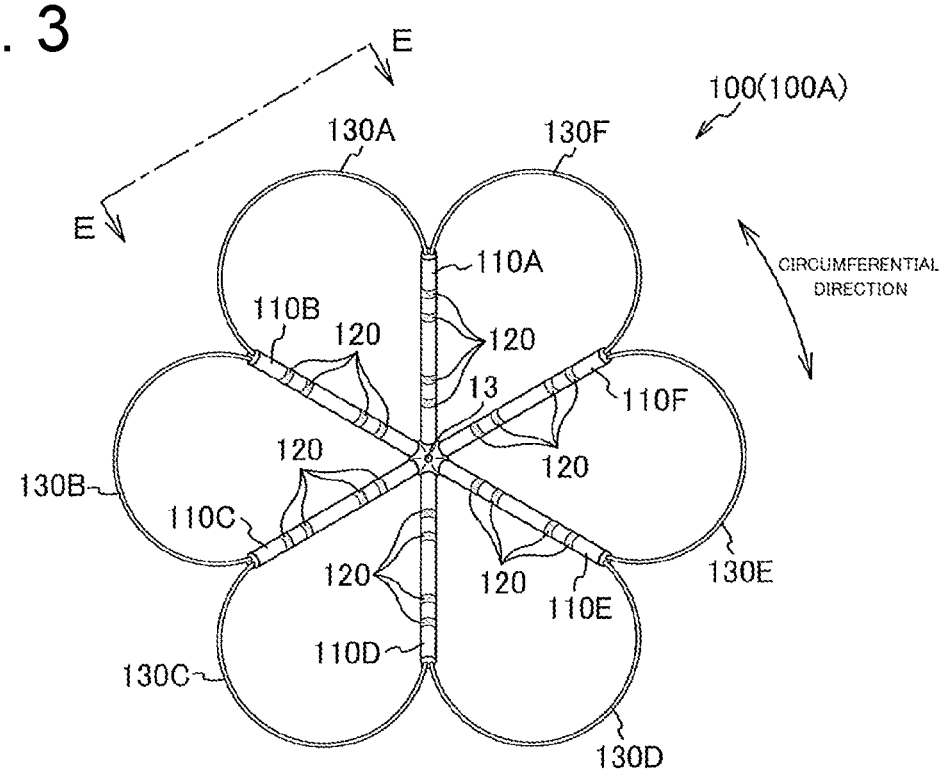
FIG. 3 is a diagram illustrating a state of an electrode unit section of the electrode catheter illustrated in FIG. 1 as observed from a direction indicated with an arrow C in FIG. 1.

FIG. 2 is a perspective view illustrating a distal-end portion of the electrode catheter illustrated in FIG. 1. FIG. 3 is a diagram illustrating a state of an electrode unit section of the electrode catheter illustrated in FIG. 1 as observed from a direction indicated with an arrow C in FIG. 1.

The electrode unit 100 (100A) includes a plurality of arm members 110 (110A to 110F) in which a one-end portion 110a in a longitudinal direction is supported by the catheter body and the other-end portion 110b in a longitudinal direction radially protrudes from the distal-end portion 10a of the catheter body 10, the ring-shaped electrodes 120, 120, onwards attached to the arm members 110, and core wires (regulating units) 130 (130A to 130F) that regulate actions of the adjacent arm members 110.

The electrode unit 100A includes six arm members 110A to 110F arranged in a circumferential direction around an axial line D (an axial line D of the electrode catheter 1) extending in the longitudinal direction of the catheter body 10. The electrode unit 100A includes six core wires 130A to 130F. Each core wire 130 connects between two arm members 110 and 110 adjacent to each other in the circumferential direction. Specifically, each core wire 130 connects between the other ends (distal ends) of two arm members 110 and 110. That is, the electrode unit 100A includes the same number of core wires 130 as the number of arm members 110.

<<Arm>>

Figure 4:
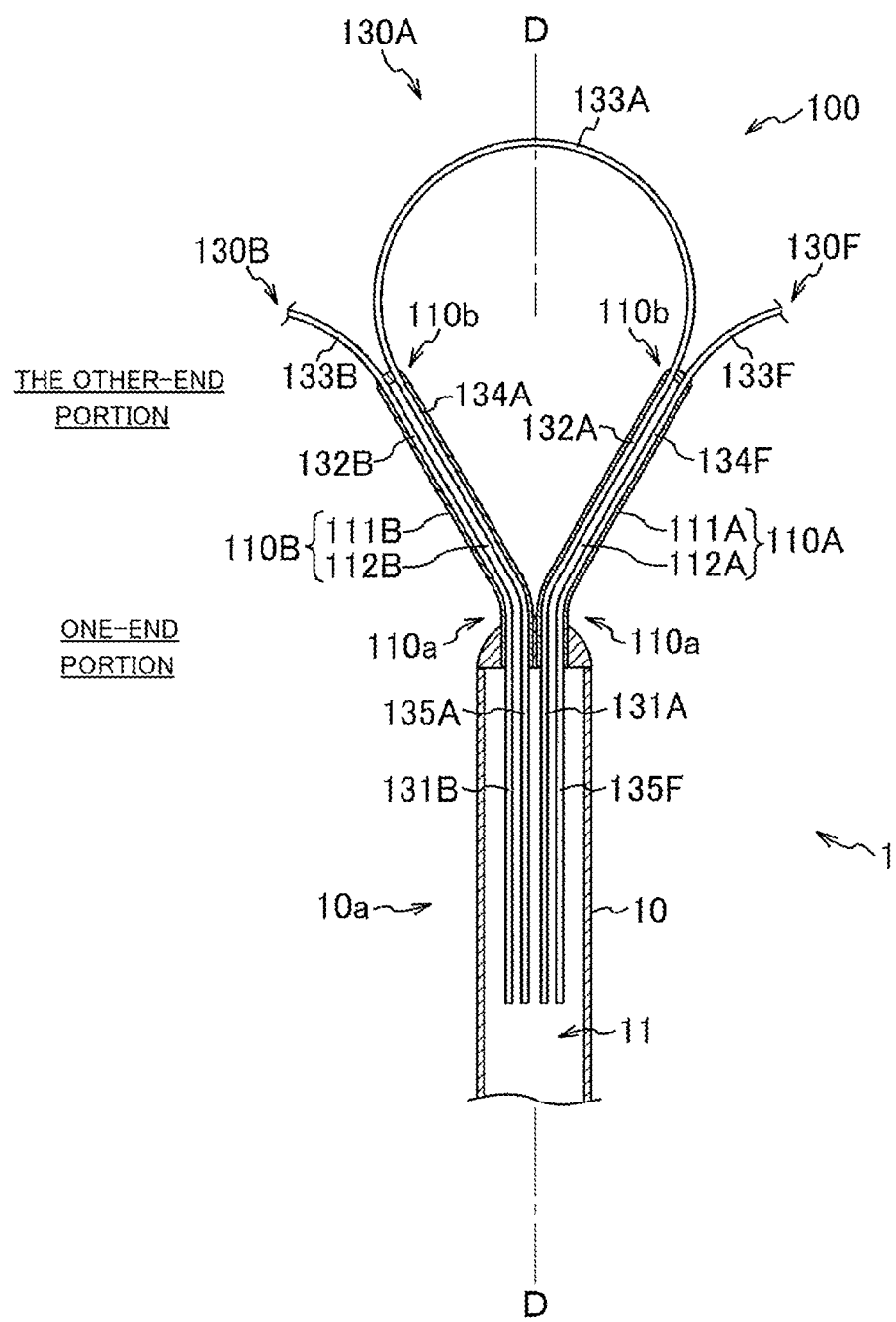
FIG. 4 is a vertical cross-sectional view illustrating a state of the distal-end portion of the electrode catheter illustrated in FIG. 1 taken along a line E-E in FIG. 3.

FIG. 4 is a vertical cross-sectional view illustrating a state of the distal-end portion of the electrode catheter illustrated in FIG. 1 taken along a line E-E in FIG. 3.

The arm members 110 (110A, 110B, . . . ) include covering tubes 111 (111A, 111B, . . . ) with hollow holes 112 (112A, 112B, . . . ) extending in a longitudinal direction. The covering tubes 111 are formed of a flexible material. Specifically, synthetic resin such as polyolefin, polyamide, polyether polyamide, polyurethane, nylon, and PEBAX (registered trademark. Substance name: polyether block amide) can be used as the covering tubes 111. The covering tubes 111 are fixed to the distal-end portion 10a of the catheter body 10 using a method such as fusion bonding.

The outer diameters of the arm members 110 are preferably in a range of 0.5 to 1.0 mm and more preferably in a range of 0.6 to 0.8 mm. The lengths of the arm members 110 in the longitudinal direction are preferably in a range of 5 to 30 mm and more preferably in a range of 10 to 20 mm. The angles of the arm members 110 with respect to the axial line D are preferably in a range of 25 to 90 degrees and more preferably in a range of 30 to 80 degrees.

Each of the arm members 110 has, at its outer circumferential portion, a plurality (four in this case) of ring-shaped electrodes 120, 120, onwards that are arranged to be separated from each other in the longitudinal direction of the arm member 110. The ring-shaped electrodes 120, 120, onwards are means for acquiring a potential in a heart and are formed of, for example, a conductive material such as platinum. Conductive wires (not illustrated) conducted to the ring-shaped electrodes 120, 120, onwards are inserted through the hollow holes 112 of the covering tubes 111. The number of ring-shaped electrodes 120 of each of the arm members 110 is an example. The number of ring-shaped electrodes 120 of each of the arm members 110 may be larger than the example or may be smaller than the example.

<<Core Wires>>

At least one core wire 130 is inserted through each of the covering tubes 111 constituting the arm members 110 in a longitudinal direction of the covering tube 111. Two core wires 130 and 130 are inserted in each of the overall arm members 110 described in this example in the entire longitudinal direction of the arm member 110.

For example, as illustrated in FIG. 4, one portion 132A of one core wire 130A in a longitudinal direction is covered with the covering tube 111A constituting the arm member 110A, while the other portion 134A of the core wire 130A in the longitudinal direction is covered with the covering tube 111B constituting the arm member 110B. That is, the one portion 132A of the core wire 130A is held by the arm member 110A, while the other portion 134A of the core wire 130A is held by the arm member 110B. The one portion 132A of the core wire 130A extends along the other portion 134F of the other core wire 130F, while the other portion 134A in the longitudinal direction extends along one portion 132B of the other core wire 130B.

An intermediate portion 133A of the core wire 130A is positioned between the one portion 132A in the longitudinal direction and the other portion 134A in the longitudinal direction and is independent from the other core wires 130B and 130F. The intermediate portion 133A protrudes beyond distal ends of the arm members 110A and 110B. Since the intermediate portion 133A is positioned on the outer side with respect to the distal ends of the arm members 110, the intermediate portion 133A can prevent the distal ends of the arm members 110 from pressing the inner wall of a heart and giving unnecessary stimulation to the heart. Further, the intermediate portion 133A is curved with a predetermined curvature in a convex shape and thus can be elastically deformed. Therefore, even when the intermediate portion 133A contacts the inner wall of the heart, due to the cushion effect of the intermediate portion 133A, it is possible to prevent the distal ends of the arm members 110 from giving unnecessary stimulation to the heart.

Each of end portions (a one-end portion 131A and the other-end portion 135A) of the core wire 130A in the longitudinal direction is held at an appropriate position of the distal-end portion 10a of the catheter body 10. Therefore, the portions (132A to 134A) of the core wire 130A forming the electrode unit 100 are formed in a loop shape.

Distal-end openings of the arm members 110A and 110B are sealed with, for example, a resin material such as silicon rubber, epoxy, or polyurethane. The core wire 130A is fixedly attached to the resin material with which the distal-end openings of the arm members 110A and 110B are sealed.

Configurations of the other core wires 130B to 130F are the same as the configuration of the core wire 130A.

Each of the core wires 130 is formed of a material having a shape memory property and a superelastic property. For example, each of the core wires 130 is formed of a nitinol wire. The core wires 130 maintain an initial shape (or an opening shape, see FIG. 2) of the electrode unit 100. In a state in which an external force is not applied to the electrode unit 100, the electrode unit 100 is in the initial shape in which the arm members 110A to 110F spread radially. The initial shape is a flower shape or a star shape.

The outer diameters of the core wires 130 are preferably in a range of 0.07 to 0.5 mm and more preferably in a range of 0.1 to 0.3 mm.

The lengths of the core wires 130 protruding from the distal ends of the arm members 110 are preferably in a range of 5 to 30 mm and more preferably in a range of 10 to 20 mm.

The intermediate portion 133A of the core wire 130A described in this example is exposed from the distal ends of the arm members 110A and 110B and is not covered with the covering tubes 111A and 111B. However, the intermediate portion 133A of the core wire 130A may be covered with the covering tubes 111. When the intermediate portion 133A is covered with the covering tubes 111, a ring-shaped electrode 120 may be attached to the corresponding portion. The same applies to the other core wires 130B to 130F.

<<Actions>>

Figure 5A:
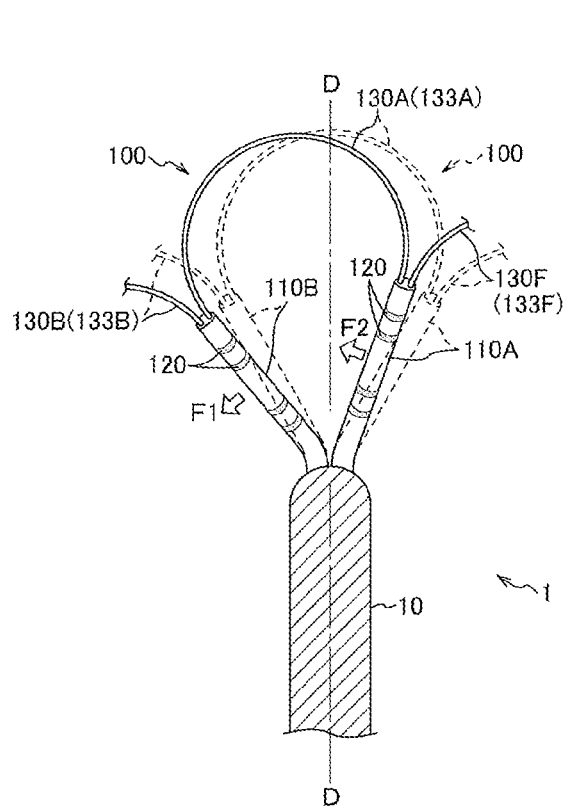
FIGS. 5(a) and 5(b) are schematic diagrams respectively illustrating a deformed state of the electrode unit section of the electrode catheter illustrated in FIG. 1.
Figure 5B:
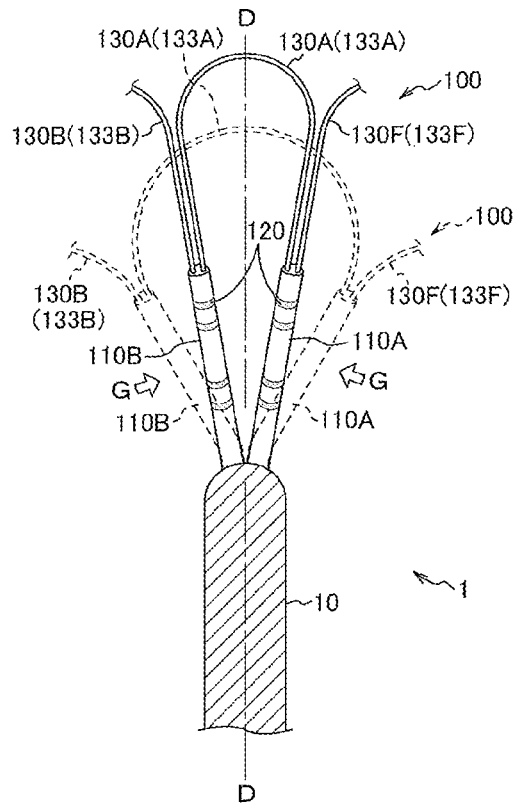

FIGS. 5(a) and 5(b) are schematic diagrams respectively illustrating a deformed state of the electrode unit section of the electrode catheter illustrated in FIG. 1. In FIG. 5, solid lines indicate shapes after deformation and broken lines indicate an initial shape. FIG. 5 illustrate a state of the electrode unit 100 as observed from the same direction as FIG. 4 and representatively illustrate actions of the two arm members 110A and 110B and the core wire 130A.

As illustrated in FIG. 5(a), when an external force F1 (an external force F1 directed in a circumferential direction) is applied to the arm member 110B to separate the arm member 110B from the arm member 110A, the arm member 110A moves toward the direction (the circumferential direction) indicated with an arrow F2 in FIG. 5(a) while following the arm member 110B. In this manner, the core wire 130A functions as a regulating unit that regulates actions of the two arm members 110A and 110B that are connected to each other via the core wire 130A. In other words, the core wire 130A functions as means for prohibiting the arm members 110A and 110B that are adjacent to each other in the circumferential direction from acting independently.

The electrode catheter 1 according to the present embodiment includes the core wires 130 as regulating units. For example, even when the electrode unit 100 is rotated around the axial line D of the catheter body 10, the core wires 130 can prevent the arm members 110 that are adjacent to each other in the circumferential direction from closely contacting each other. Therefore, it is possible to prevent unintended concentration of the radially protruding arm members 110.

As illustrated in FIG. 5(b), when an external force G (an external force G directed from the outer side toward the inner side in a radial direction) directed toward the axial line D of the electrode catheter 1 is applied to the electrode unit 100, the electrode unit 100 is deformed in such a manner that curvatures of the core wires 130A to 130F increase corresponding to the magnitude of the external force G. Thereafter, the electrode unit 100 takes a converged shape (a concentrated shape) in which the arm members 110A to 110F are concentrated on the axial line D side and are close to each other. The electrode unit 100 in the converged shape can be advanced and retracted in a cylindrical sheath that guides the electrode unit 100 section to a heart.

On the other hand, when an external force (an external force directed from the inner side toward the outer side in the radial direction) is applied to the electrode unit 100 to separate the arm members 110A to 110F from the axial line D, the electrode unit 100 takes a shape in which the arm members 110A to 110F are further separated from the axial line D than the initial shape. In this case, the core wires 130A to 130F are deformed in such a manner that the curvatures of the core wires 130A to 130F decrease corresponding to the magnitude of the applied external force. In the electrode unit 100, the length of the intermediate portion 133A of the core wire 130 is set to be longer than the distances between the distal ends of the arm members 110, 110 when the electrode unit 100 is in the initial shape, and thus the deformation that causes the distal ends of the arm members 100 to be further separated is acceptable.

When the external force illustrated in FIGS. 5(a) and 5(b) is eliminated, the electrode unit 100 returns to the initial shape indicated by the broken lines due to the shape memory property and superelastic property the core wires 130 have. The initial shape or the shape in which the arm members 110A to 110F are more separated than the initial shape is a shape when the electrode unit 100 measures an intracardiac potential or the like and can collectively and simultaneously acquire intracardiac potentials at many points, that is, a shape that the electrode unit 100 can perform mapping at many points simultaneously.

The core wires 130 not only function as regulating units that regulate actions of the adjacent arm members 110, but also maintain the initial shape of the electrode unit 100 and function as means for causing the electrode unit 100 to return to the initial shape after deformation of the electrode unit 100. The electrode unit 100 can be downsized by providing each of the core wires 130 with multiple functions, as compared to the case where the same functions are realized by a plurality of members.

Modified Embodiment

Figure 6A:
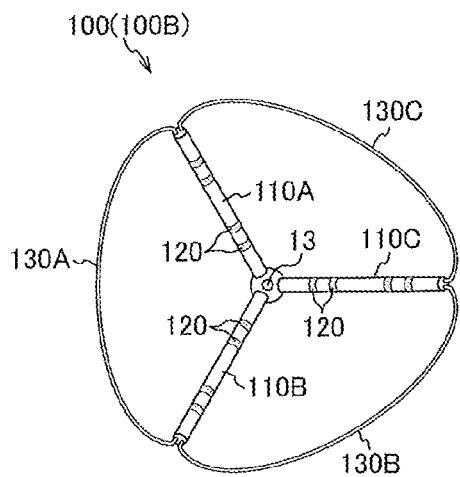
FIGS. 6(a) and 6(b) are schematic diagrams respectively illustrating an electrode unit section of an electrode catheter according to a modified embodiment of the present invention.
Figure 6B:
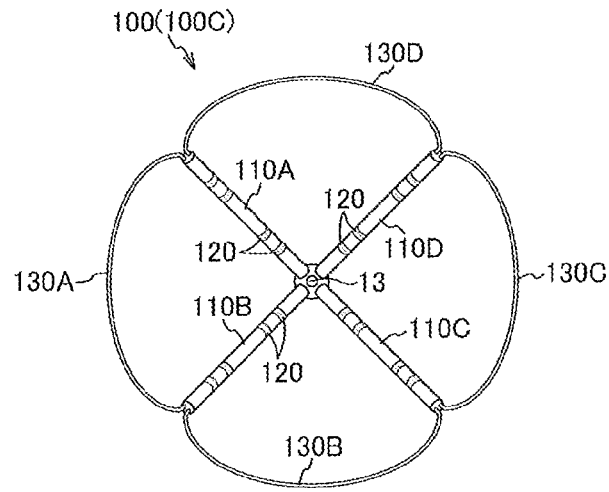

FIGS. 6(a) and 6(b) are schematic diagrams respectively illustrating an electrode unit section of an electrode catheter according to a modified embodiment of the present invention. FIG. 6 are diagrams that correspond to diagrams viewed from the arrow C in FIG. 1. Like reference signs are denoted to constituent elements identical to those of the first embodiment, and explanations thereof are omitted as appropriate.

FIG. 6(a) is a diagram illustrating an example of an electrode unit 100B having three arm members 110A to 110C and three core wires 130A to 130C. FIG. 6(b) is a diagram illustrating an example of an electrode unit 100C having four arm members 110A to 110D and four core wires 130A to 130D.

The number of arm members 110 included in the electrode unit 100 and the number of core wires 130 included in the electrode unit 100 can be set freely to some extent as long as the numbers are acceptable for an inner diameter of a sheath placed in a blood vessel when an electrode catheter is inserted in the blood vessel.

[Summary of Actions and Effects of Aspects in the Present Invention]

<First Aspect>

In the present aspect, the electrode catheter 1 includes the catheter body 10 and the electrode unit 100 attached to the distal-end portion 10a of the catheter body. The electrode unit includes a plurality of arm members 110 in which a one-end portion 110a in a longitudinal direction is supported by the catheter body and the other-end portion 110b in a longitudinal direction radially protrudes from the distal-end portion of the catheter body, electrodes (the ring-shaped electrodes 120) attached to the arm members, and regulating units (the core wires 130) that regulate actions of the adjacent arm members.

According to the present aspect, since the regulating units regulate actions of adjacent arm members, it is possible to prevent unintended concentration of the radially protruding arm members.

<Second Aspect>

In the electrode catheter 1 according to the present aspect, each of the regulating units (the core wires 130) connects between distal ends of two adjacent arm members among the arm members 110, 110 and protrudes beyond the distal ends of the arm members.

According to the present aspect, the regulating units protrude beyond the distal ends of the arm members, and thus it is possible to prevent the distal ends of the arm members from pressing the inner wall of a heart and giving unnecessary stimulation to the heart.

<Third Aspect>

In the electrode catheter 1 according to the present aspect, at least one of the regulating units (the core wires 130) is inserted through each of the arm members 110 in the longitudinal direction of the arm member, and the regulating units maintain an initial shape of the electrode unit 100.

In the present aspect, the regulating units not only function as means for regulating actions of adjacent arm members, but also function as means for maintaining the initial shape of an electrode unit. The electrode unit can be downsized by providing each of the regulating units with multiple functions, as compared to the case where the same functions are realized by a plurality of members.

<Fourth Aspect>

In the electrode catheter 1 according to the present aspect, when an external force G directed from the outer side toward the inner side in the radial direction is applied to the electrode unit 100, the electrode unit 100 takes a converged shape (see the solid lines in FIG. 5(b)) in which the arm members 110 are close to each other, and when the external force is eliminated, the electrode unit 100 returns to an initial shape (see the broken lines in FIG. 5(b), FIG. 2, and the like) in which the arm members spread radially.

According to the present aspect, the electrode unit can be deformed into a converged shape so as to be advanced and retracted in a sheath. Further, when the electrode unit is detached from the sheath, the electrode unit returns to the initial shape and thus the electrode unit can collectively and simultaneously acquire intracardiac potentials at many points.

REFERENCE SIGNS LIST 1 electrode catheter, 10 catheter body, 10a distal-end portion, 11 lumen, 13 perfusion port, 20 operating unit, 21 handle, 22 rotating plate, 100, 100A-100C electrode unit, 110, 110A-110F arm member, 110a one-end portion, 110b the other-end portion, 111, 111A, 111B covering tube, 112, 112A, 112B hollow hole, 120 ring-shaped electrode, 130, 130A-130F core wires (regulating units), 131 one-end portion, 132 one portion, 133 intermediate portion, 134 the other portion, 135 the other-end portion.

The invention claimed is:

1. An electrode catheter comprising:
a catheter body having a longitudinal axis; and
an electrode unit attached to a distal end portion of the catheter body including a plurality of arm members having electrodes attached thereto and a plurality of regulating units to regulate actions of adjacent ones of the arm members of the plurality of arm members;
wherein each of the plurality of arm members comprises a proximal portion supported by the catheter body in a longitudinal direction and a distal end portion radially protruding from the distal end portion of the catheter body; and
wherein each of the plurality of regulating units is inserted through a proximal portion and extends beyond a distal portion of a respective arm member of the plurality of arm members into a distal and proximal portions of an adjacent arm member of the plurality of arm members to connect between the distal ends of the respective and adjacent arm members such that each of the arm members comprises two respective regulating units of the plurality of regulating units.

2. The electrode catheter according to claim 1, wherein the plurality of regulating units maintain an initial shape of the electrode unit.

3. The electrode catheter according to claim 2, wherein when an external force directed from an outer side toward an inner side in a radial direction is applied to the electrode unit, the electrode unit takes a converged shape in which the plurality of arm members are close to each other, and when the external force is eliminated, the electrode unit returns to the initial shape in which the plurality of arm members spread radially.

* * * * *